United States Patent [19]
Waknine et al.

[11] Patent Number: 5,348,475
[45] Date of Patent: Sep. 20, 1994

[54] TRIMODAL METHOD OF CURING DENTAL RESTORATIVE COMPOSITIONS

[75] Inventors: Samuel Waknine, Branford; Arun Prasad, Cheshire; Weitao Jia, Wallingford, all of Conn.

[73] Assignee: Jeneric/Pentron Inc., Wallingford, Conn.

[21] Appl. No.: 51,444

[22] Filed: Apr. 22, 1993

Related U.S. Application Data

[63] Continuation of Ser. No. 697,063, May 8, 1991, abandoned.

[51] Int. Cl.$^5$ .......................... A61C 5/00; A61C 13/00
[52] U.S. Cl. .......................... 433/215; 264/16; 264/19; 264/22; 264/102; 264/236; 264/347; 433/223; 433/228.1
[58] Field of Search .......................... 264/16, 17, 22, 19, 264/102, 101, 236, 347, 571; 522/1, 3, 908, 915; 433/223, 226, 228.1, 215

[56] References Cited

U.S. PATENT DOCUMENTS

| | | | |
|---|---|---|---|
| 4,045,867 | 9/1977 | Ström | 29/628 |
| 4,073,835 | 2/1978 | Otsuki et al. | 264/22 |
| 4,233,396 | 11/1980 | Armstrong et al. | 430/320 |
| 4,411,625 | 10/1983 | Koblitz et al. | 433/217 |
| 4,544,359 | 10/1985 | Waknine | 523/115 |
| 4,547,531 | 10/1985 | Waknine | 523/116 |
| 5,190,702 | 3/1993 | Johnson | 264/16 |

OTHER PUBLICATIONS
Japanese Abstract 83-811869/45, Mar. 29, 1982.

*Primary Examiner*—Jan H. Silbaugh
*Assistant Examiner*—Christopher A. Fiorilla
*Attorney, Agent, or Firm*—Kramer, Brufsky & Cifelli

[57] ABSTRACT

A trimodal method of curing dental composite restorative materials involves the use of visible light illumination for the initial curing of the composite resin and a combination of dry heat and vacuum for the complete cure of the composite restorative materials. More specifically, the method for preparing dental restorative materials includes the steps of forming a dental restoration from a composite resin of a type conventionally employed in the dental profession, in which the composite resin includes a photosensitizing system for initiating polymerization of the composite resin upon exposure to visible light, an initiator for initiating polymerization upon application of heat and at least one filler; exposing the thus prepared restoration to a source of visible light to at least partially cure said composite resin and then subjecting the thus prepared restoration to a combination of heat and vacuum to complete polymerization of said complete resin.

7 Claims, No Drawings though incomplete cure of the restorative dental resin or composite and produce a restoration having less than optimum mechanical and physical properties. Dental restorations formed by heat and pressure curing of composite resins also often exhibit inferior properties. In addition, dental laboratories which prepare dental restorative materials by heat and pressure cure require high pressure polymerization pots or containers, which are dangerous to use. Chemical initiation systems are highly inflexible as a result of the occurrence of rapid polymerization upon mixture of the two components and void inclusion. As a result, there has been a perceived need in the dental profession for a curing methodology which would result in an aesthetic dental restoration exhibiting superior properties, which is also safe and easy to use.

TRIMODAL METHOD OF CURING DENTAL RESTORATIVE COMPOSITIONS

This application is a continuation of application Ser. No. 07/697,063, filed May 8, 1991 now abandoned.

FIELD OF THE INVENTION

The present invention relates to a method of preparing dental restorative composite materials exhibiting superior toughness, versatility and esthetics and also relates to the dental restorative materials prepared in accordance with the method.

BACKGROUND OF THE INVENTION

The practice of dentistry includes the preparation and application in the oral environment of artificial tooth structures and restorations. Such restorations include, for example, veneers, inlays, onlays, crowns and bridges. Historically, the dental profession has used several different types of materials for aesthetic restorative purposes. Unfilled acrylic resins, silicate cements and direct fill resins have all been used. Dental composite materials, which are particularly preferred for the purpose of aesthetic restorations, include an inorganic filler component such as glass and an organic matrix component such as a polymerizable monomer. Such composites typically comprise an acrylic or methyacrylic based system in which a silica or silicate glass is bonded to the resin matrix or to a coupling agent which is bonded to both.

Dental restorations are typically prepared by forming a restorative structure from an appropriate resin or composite material in the oral cavity or by placing the appropriate resin or composite material on a laboratory working model die made from an intra-oral impression replica or alloy substrate and curing the restorative material. The composite materials currently in use for such restorations involve the conversion of monomers and/or oligomers into a polymerization matrix by chemical or photochemical initiation to form free radicals and thereby effect polymerization.

Chemical initiation is generally effected by admixing substantially equal amounts of two paste or powder/liquid systems, one containing an initiator—usually peroxide or other free radical generating material and the other containing an organic amine accelerator -which react to produce free radicals and thereby initiate the polymerization reaction.

The light curing systems are based upon the discovery that certain chemical compounds will initiate polymerization of component monomeric units when exposed to light waves, in either the ultra violet or visible light region of the spectrum. U.S. Pat. No. 4,411,625, for example, describes composite dental restorative compositions which are curable by the action of light having visible and/or UV components. Photochemical initiation provides the ultimate flexibility in placement and working with the restoration since the monomers and/or oligomers are substantially unreactive until exposed to an appropriate light source which initiates polymerization.

Heat and pressure cure systems are also used in the conversion of monomers and/or oligomers into a polymeric matrix for dental restorations.

Although the foregoing modalities of cure have been extensively used and are currently in widespread practice in the dental profession, it has been found that each exhibits certain disadvantages. For example, visible light curing techniques frequently result in incomplete cure of the restorative dental resin or composite and produce a restoration having less than optimum mechanical and physical properties. Dental restorations formed by heat and pressure curing of composite resins also often exhibit inferior properties. In addition, dental laboratories which prepare dental restorative materials by heat and pressure cure require high pressure polymerization pots or containers, which are dangerous to use. Chemical initiation systems are highly inflexible as a result of the occurrence of rapid polymerization upon mixture of the two components and void inclusion. As a result, there has been a perceived need in the dental profession for a curing methodology which would result in an aesthetic dental restoration exhibiting superior properties, which is also safe and easy to use.

Accordingly, it is an object of the present invention to provide a novel method of preparing dental restorative materials which overcomes the deficiencies of the prior art systems.

It is another object of the present invention to provide a method for preparing polymerized dental restorative materials exhibiting greater fracture toughness and flexural strength and lower polymerization shrinkage than the currently available heat/pressure cure materials and the visible light cured materials in order to nullify post-operative sensitivity, improve marginal integrity and fracture and wear resistance.

A still further object of the invention is to provide a dental restoration prepared in accordance with the novel methodology.

SUMMARY OF THE INVENTION

These as well as other objects and advantages are achieved in accordance with the present invention, which provides a trimodal method of curing dental composite restorative materials. The method involves the use of visible light illumination for the initial curing of the composite resin and a combination of dry heat and vacuum for the complete cure of the composite restorative materials. More specifically, the method for preparing dental restorative materials comprises the steps of forming a dental restoration from a composite resin of a type conventionally employed in the dental profession, in which the composite resin includes a photosensitizing system for initiating polymerization of the composite resin upon exposure to visible light, an initiator for initiating polymerization upon application of heat and at least one filler; exposing the thus prepared restoration to a source of visible light to at least partially cure said composite resin and then; subjecting the thus prepared restoration to a combination of heat and vacuum to complete polymerization of said composite resin.

Without wishing to be held to any particular theory of the invention, it is believed that this unique curing technique yields a polymer chain structure orientation or order near the glass transition temperature and generates a semi-crystalline network without physical deformation of the restoration. The consequence is a polymerized material with significantly greater fracture toughness, impact strength and flexural strength, i.e. a rigid and tough material with greater fatigue and wear resistance than prior art systems. The restorations prepared in accordance with the inventive method also exhibit an inherently lower polymerization shrinkage when compared to the commercially available heat and pressure cure restorative materials and the visible light and vacuum cure materials.

DETAILED DESCRIPTION OF THE INVENTION

The dental restorative compositions useful in the methodology of the present invention are not particularly limited and comprise broad spectrum polymer blends comprising binder resins, diluent monomers, fillers, a photosensitizing system and a heat cure system. The blends may also optionally include antioxidants, shelf life stabilizers, pigments, opacifiers, handling agents and other modifiers as will be readily appreciated by those of skill in the art.

The dental restorative composition will comprise at least one binder resin. Binder resins particularly useful in the method of the present contain a polycarbonate dimethacrylate as a principal component. As used herein, the term "polycarbonate dimethacrylate" describes a polycarbonate dimethacrylate condensation product obtained by the condensation reaction of an hydroxyalkylmethacrylate of the general formula I

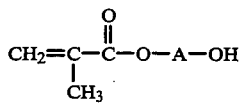

in which A is $C_1$–$C_6$ alkylene, and a bis(chloroformate) of the general formula II

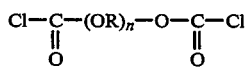

in which R is $C_2$–$C_5$ alkylene having at least two carbon atoms in its principal chain and n is an integer from 1 to 4. By "principal chain" is meant the chain of carbon atoms serving as a bridge between the oxygen atoms.

These materials are described in U.S. Pat. No. 5,276,068, issued Jan. 4, 1994, the pertinent portions of which are hereby incorporated by reference.

Other suitable binder resins include a wide variety of ethylenically unsaturated polymerizable compositions, including the bis-glycidyl-methacrylate adduct of bisphenol A (Bis-GMA) and its acrylic counterparts. Alternatively, the adducts of 2,2,3-trimethylhexane diisocyanate with hydroxyethyl methacrylate, hydroxypropyl methacrylate and other hydroxyalkyl acrylic species are also preferred. Those skilled in the art will appreciate that other acrylated polyesters may also be suitable. Such acrylated polyesters may also be reacted with isocyanates to form urethanes useful as binder resins. Thus, Bis-GMA may be reacted with a diisocyanate (or other isocyanate) such as hexamethylene diisocyanate, phenylene diisocyanate or a wide variety of other aliphatic and aromatic diisocyanates to provide useful binder resins.

A particularly preferred binder resin comprises an admixture of a polycarbonate dimethyacrylate and a second resin, such as Bis-GMA or urethane dimethacrylate, or oligomers thereof, wherein the polycarbonate dimethacrylate comprises the condensation product of triethylene glycol bis(chloroformate) and 2-hydroxyethyl methacrylate.

The dental restorative composition will also typically include a diluent monomer to increase the surface wetability of the composition by decreasing the viscosity of the polymerization medium and increasing the contact angle of the droplet in order to attain a more manageable unfilled or filled working viscosity. Further, such diluents are used as crosslinking agents.

Viscosity control which is well within the skill of the art will be understood to result in moldable, workable materials suitable for a wide range of dental restorative uses. Diluent monomers may be any of a wide range of polymerizable monomers capable of sustaining photochemically and heat initiated polymerization. Preferably, the diluents will be the hydroxyalkyl methacrylates such as 2-hydroxyethylmethacrylate and 2-hydroxypropylmethacrylate; ethylene-glycolmethacrylates, including ethyleneglycolmethacrylate, diethyleneglycolmethacrylate, triethyleneglycolmethacrylate and tetraethyleneglycolmethacrylate; diisocyanates, hexamethylene diisocyanate and ethoxylated monomers such as 1,6-hexanedioldimethacrylate. 2-hydroxyethylmethacrylate (2-HEMA) and/or triethylenedimethacrylate (TEGDMA) are particularly preferred.

The fillers utilized in the dental restorative compositions of the present invention can be selected from any of the fillers conventionally used in the dental industry capable of being covalently bonded to the resin matrix itself or to a coupling agent which is covalently bonded to both. Among those fillers which are especially suited in the practice of this invention are the alkali metal or alkaline earth metal silicates, such as lithium silicate, barium silicate and the like. Other examples of suitable filling materials include, but are not limited to, silica, silicate glass, quartz, strontium silicate, borosilicate, amorphous silica and alumina, zirconia, and tin oxide. Particularly suitable fillers for dental restorative materials prepared in accordance with the present invention are those having a particle size ranging from about 0.1–5.0 μm with a silicate colloid of 0.001 to about 0.07 μm and prepared by a series of milling steps comprising wet milling in an aqueous medium, surface etch milling and silanizing milling in a silane solution. Some of the aforementioned inorganic fillers are described in U.S. Pat. Nos. 4,544,359 and 4,547,531, the pertinent portions of which are hereby incorporated by reference.

Those skilled in the art will appreciate that the amount of filler loading which may be accomplished with a given resin system will vary depending upon several factors including identity of the resins and fillers and the particle sizes of the filler. It should be appreciated that, for a given resin system, an appropriate filler must be chosen. For example, the filler selected must be such that the transmission of visible or ultraviolet light by the restorative composition must be sufficient for polymerization to take place. Persons skilled in the art will be able to select fillers and determine filler particle sizes based upon this requirement.

The dental restorative compositions of the present invention must include a photosensitizing system for inducing polymerization of the resin monomers and/or oligomers by the action of visible light. The polymerization initiators usable in the dental restorative compositions are conventional visible light cure initiators well known in the art. Light sensitive compounds such as benzyl, diketones and dl camphoroquinone are preferred, with the camphoroquinone being particularly preferred.

The dental restorative composition will also include an organic tertiary amine reducing agent as a visible light polymerization accelerator. Numerous tertiary amines are useful as reducing agents for inclusion in the present invention, however, the tertiary amines are generally acrylate derivatives such as dimethylaminoethylmethacrylate and diethylaminoethylmethacrylate.

The dental restorative composition of the present invention further includes an initiator for heat curing in the second curing step of the inventive method. Any of the self curing peroxides well known to those of skill in the art can be used as the heat cure initiator, with benzoyl peroxide (BPO) being particularly preferred.

Pigments, ultraviolet light absorbers, opacifiers, brightening agents and antioxidants/shelf life stabilizers, i.e., BHT, and other modificants may be included in the restorative compositions of the invention without departing from its spirit.

The method of preparing composite dental restorations in accordance with the present invention involves the preparation of the restoration from the composite resin in accordance with known techniques, at least partially curing the restoration with visible light and then completing the cure of the restoration with a heat/vacuum cure step. The restoration can be prepared in one step, or in a series of layering steps. In the preparation of veneers, inlays, onlays, crowns and bridges and the like, the restoration is preferably prepared from a series of layers of an appropriate composite dental restorative material and each layer is light cured for about 20–60 seconds, preferably about 40 seconds per tooth aspect: occlusal, proximal, facial and lingual. Partial hardening of each layer by exposure to visible light is required, since the composite pastes/resins, by themselves, do not offer the resistance essential for build-up. Layering in this fashion, wherein the various layers are formulated to reflect natural tooth structure, results in the most natural and aesthetically pleasing restorations. Formulation of the composite restorative materials to reflect natural tooth structure has become conventional and is within the skill of the art. In general, the portion of the restoration overlying the dentin will be more opaceous than the body of the tooth structure, which is formulated to resemble the tooth enamel. Cusp tips and incisals are relatively transparent and the composite resin layers which will make up this aspect of the restoration will be formulated accordingly. Stratification of opacity/translucency partakes with dentin, enamel, incisal, cervical and effect pastes with intermittent stain characterization.

The preparation of the restoration can occur intraorally by the dentist, for example for simple inlays and onlays, or extraorally by a dental laboratory, on a stone model or rigid polyvinylsiloxane made from an intraoral impression replica or onto an alloy substrate (foil or cast) in various layers.

When building a restoration intraorally or on a working model, a releasing agent is applied onto the tooth structure or model, respectively, overlapping the cavosurface margin. As an optional technique, the restoration should be removed from the model after each layer is built up and cured, and the releasing agent reapplied before the addition of the next layer, being careful not to entrap release agent between composite layers. Suitable releasing agents include a combination of mineral oil and methanol, hydrophilic silicon-type surfactants or various hydrophilic oil lubricants.

Upon completion of the restoration, the restoration can be trimmed and polished in accordance with well established techniques, after which the restoration is subjected to a further curing step. This curing step involves subjecting the restoration to dry heat under vacuum (i.e. an oxygen inhibited environment) for sufficient amount of time to effect complete curing of the composite resin. More specifically, the restoration is placed into a heat/vacuum chamber, either with or without the die, which has been preheated to the appropriate temperature and the chamber is evacuated for a period of time ranging from about 10 to about 30 minutes, preferably from about 10–20 minutes. The curing is effected at a temperature which is at or near the glass transition temperature of the composite dental restorative material. A temperature of 225° F. (107° C.) is preferred, but is not limiting. The pressure within the vacuum chamber should be from about 27 to about 29.5 in. Hg, and preferably is maintained at about 28.5–29.5 in. Hg during the curing process. This anaerobic environmental chamber near Tg attains a greater Dp and polymer chain orientation leads to further semicrystallinity attaining greater toughness and rids of residual surface monomeric layers.

The CONQUEST curing oven, available from Jeneric/Pentron, Inc. of Wallingford, Conn., is particularly well suited for the heat/vacuum curing, although other suitable heat/vacuum chambers may also be employed.

Upon removal from the heat/vacuum oven, the restoration should be bench hardened for at least several minutes prior to further handling. Preparation of the restoration for placement in the oral environment is in accordance with conventional techniques, for example by sand blasting the interior surface of the restoration with aluminum oxide, using wax or a rubber-sep type product to protect the glaze finish. The thus-prepared restorations can be bonded intraorally using any of the commercially available bonding agents resin luting cement systems, selection of which is well within the skill of the art.

The present invention will be more clearly understood from the following specific examples.

EXAMPLE I

This example provides the formulation for a dental restorative composition particularly suitable for use in accordance with the methodology of the present invention. The composition comprises:

From about 15–40% by weight of a resin matrix comprising:
- 20–60 grams of polycarbonate dimethacrylate, which is the polycondensation reaction product of 2-hydroxyethlymethacrylate and triethylene glycol bis(chloroformate);
- 15–40 grams of Bis-GMA/UDMA;
- 0–40 grams of 2-hydroxyethylmethacrylate/TEGDMA;
- 0.05–0.20 grams d,l camphoroquinone (Visible light cure initiator);
- 0.05–0.20 grams benzil (Visible light cure initiator);
- 0.20–0.50 grams diethylaminoethylmethacrylate (visible light cure accelerator);
- 0.4–4.0 grams benzoyl peroxide (heat cure initiator);
- 0.01–0.15 grams of benzoylhydroxytoluidine (BHT);
- 0.5–1.5 grams of TINUVIN P or Tinuvin 328 (ultraviolet absorber from Ciba-Geigy Corporation, Ardsley, N.Y.), or UV-9, UV-5411 (from Cyanamid, Wayne, N.J.);
- 0.005–0.5 grams of UVITEX OB (fluorescent whitening agent from Ciba-Geigy Corporation, Ardsley, N.Y.);
- 0.1–2.0 grams of Tinuvin 292 (HALS, Hindred amine light stabilizer from Ciba-Geigy, Corp., Ardsley, N.Y.) in admixture with from about 40–95% by weight of barium borosilicate, 1–15 weight % γ-methacryloxypropyltrimethoxysilane and 1–50 weight % of colloidal amorphous silica as filler, such that a 100% filled polymer resin system is obtained.

EXAMPLE 2

This example demonstrates that the consequence of using the methodology of the present invention is a polymerized dental restorative material with significantly greater fracture toughness, impact strength, flexural strength and wear resistance, i.e. a rigid and tough material with greater fatigue resistance than heretofore achieved with the prior art systems.

In this example, the dental restorative composite systems utilized included (1) Indirect and (1) Direct-Indirect, Concept (Vivadent/Ivoclar/Williams Co.) and Conquest C/B (Jeneric/Pentron, Inc.) accordingly.

The Concept system undergoes an indirect preparation process by curing the composite in an Ivomat chamber (Buffalo, N.Y.) in water at 250° F. and 85 psi air pressure.

The Conquest C/B system undergoes a Direct/Indirect preparation process by first curing the composite with a visible light curing gun apparatus for 40 seconds per layer (Optilux 400, Demetron Corp., Danbury, Conn., or Litex 660, Jeneric/Pentron, Wallingford, Conn.) and then a secondary cure process takes place in the Conquest curing oven unit at 225° F. under vacuum 29 in. Hg. Dental restorative composites were prepared and cured in accordance with the manufacturer's direction.

Other curing devices are commercially available which can polymerize the material as well, such as Visio-Gem; visible light and vacuum cure simultaneously. It is the purpose of this experimental test series to illustrate; (1) the superior mechanical properties associated with Conquest C/B vs Concept and (2) the optimum maximum mechanical properties of Conquest C/B can be attained only by the trimodal process (visible light, heat/vacuum) of curing described and claimed herein.

TEST PROTOCOL

Materials and Methods

Modulus of Rupture=Flexural Strength (MOR)
Diametral Compressive Tensile Strength (DTS)

The test samples (8) per group were prepared in accordance with ASTM #C-674-71 and ADA Spec. #27 revised 1990. The modified test sample dimensions for MOR were 3×3×50 mm breadth (b)×depth (d)×length accordingly or 0.1181×0.1181×1.9685 in. rectangular bars. Whereas the DTS samples were 6 mm diameter (d)×3 mm height (1) or 0.2362×0.1181 in. cylinders. The composite paste systems were packed and condensed into 3-way aluminum split dies, compressed with the aid of 25×75 mm rectangular microscope glass slides for MOR samples and 25×25 mm glass slides for DTS samples with finger pressure in order to attain a smooth-uniform surface and configuration. Thereafter, the glass slides were retrieved. Each set of composite paste samples were cured in accordance with the following tabulated protocol sequence and curing devices. (Table I.)

TABLE I

| Groups | Materials/ Manufacturer | Curing System/ Manufacturer | Curing Conditions |
|---|---|---|---|
| #1 | Concept/ Ivoclar Williams | Ivomat 250/ Ivoclar Williams | Heat/Pressure 250° F./85 psi Water/air |
| #2 | Conquest/ Jeneric/Pentron | Optilux 400/Demetron Ivomat 250/Ivoclar Williams | Visible light Heat/Pressure 250° F./85 psi water/air |
| #3 | Conquest/ Jeneric/Pentron | Optilux 400/Demetron | Visible light |
| #4 | Conquest/ Jeneric/Pentron | Visio Gem Curing System/ESPE-Premier | Visible light/ Vacuum |
| #5 | Conquest/ Jeneric/Pentron | Optilux 400/Demetron Conquest Curing Oven-Jeneric/Pentron | Visible light Heat/Vacuum 225° F./29 in Hg. |

The Optilux 400 light gun was used to illuminate the MOR samples 5 times at each 10 mm of the bar sample length increment (50 mm total length) for 60 sec. exposure per increment with the 13 mm light probe. The DTS specimens were exposed for one 60 sec. illumination period. The other curing devices were used as per manufacturer instructions for 15 min. automated cycles (Ivoclar, ESPE and Jeneric/Pentron). Thereafter, the dies were disassembled and composite bars were polished with a series of silicon carbides paper strips 240, 320, 400 and 600 grit (Handimet II-Buehler Corp.). The samples were aged in a 37° C. distilled water bath for 24 hours, retrieved and measured with a digital micrometer (Mitutoyo Corp.), for b, d & marked for L spacing for MOR bars and d & l for DTS samples and recorded. Then, the samples were mounted on an Instron machine with appropriate fixtures (Instron Co., Canton, Ohio) and tested in a compressive modes for MOR at 0.002 in/min. cross head speed (CHS) and for DTS at 0.2 in/min. CHS.

The equations used to calculate the MOR and DTS were:

$$MOR = \frac{3 PL}{2bd^2} = pounds/inches^2 \text{ (psi)} \qquad (1)$$

where  $P$ = load (lbs.) to fracture
 $L$ = length-distance between supports
 $b$ — breadth/width of bar sample (inches)
 $d$ — depth/thickness of bar sample (inches)

$$DTS = \frac{2P}{\pi dl} \qquad (2)$$

-continued where  P = load (lbs.) to fracture
       d = diameter of sample (inches)
       l = height of sample (inches)

The (8) samples per group were averaged and standard deviations calculated and reported in the following table. (Table II).

TABLE II

| Group | MOR psi (standard deviation) | DTS psi (standard deviation) |
|---|---|---|
| #1 | 9062 (431.85) | 13680 (1011.80) |
| #2 | 9034 (248.70) | 16250 (1292.91) |
| #3 | 8132 (429.43) | 18203 (238.97) |
| #4 | 7766 (268.10) | 17,988 (951.28) |
| #5 | 10,564 (297.93) | 23,313 (1407.10) |

The results of this experiment demonstrate that the consequence of using the methodology of the present invention in group (5) is a polymerized dental restorative material exhibiting statistically significant greater flexural strength, i.e., toughness and diametral tensile strength than achieved with other prior art systems.

From the above description it is apparent that the objects of the present invention have been achieved. While only certain embodiments have been set forth, alternative embodiments and various modifications will be apparent from the above description to those skilled in the art. Such other alternatives are considered equivalents and within the spirit and scope of the invention.

Having described the invention, what is claimed is:

1. A method for preparing a composite dental restoration exhibiting improved toughness and fracture resistance comprising the steps of:

(A) forming a dental restoration from at least one layer of a composite resin, said composite resin comprising
   (i) at least one binder resin,
   (ii) a diluent monomer,
   (iii) a photopolymerization system comprising an initiator for initiating polymerization of the composite resin upon exposure to visible light and an accelerator,
   (iv) an initiator for initiating polymerization of the composite resin upon application of heat, and
   (v) at least one filler, wherein each layer of the composite resin is exposed to a source of visible light to partially cure each layer of said composite resin to provide sufficient hardening to enable building up of additional layers of composite resin thereon;

(b) subjecting the thus prepared restoration to a combination of dry heat and vacuum sufficient to remove residual monomeric surface layers and anaerobically complete polymerization of said composite resin.

2. A method according to claim 1, wherein the dental restoration is selected from the group consisting of crowns, bridges, inlays, onlays, laminates, pre-fabricated post cores, lingual splints and bio-dental prosthetic partials.

3. A method according to claim 1, wherein the binder resin comprises a polycarbonate dimethacrylate in combination with a second resin selected from the group consisting of Bis-GMA, polyurethane dimethacrylate and oligomers thereof.

4. A method according to claim 1, wherein the photopolymerization system comprises d,l camphoroquinone as a polymerization initiator and a tertiary amine as the accelerator and said heat polymerization initiator is benzoyl peroxide.

5. A method according to claim 4, wherein the restoration is subjected to heat at a temperature of 225° F. in step (B).

6. A method according to claim 1, wherein the visible light curing in step (A) is conducted intraorally.

7. A method according to claim 1, wherein the visible light curing in step (A) is conducted extraorally.

* * * * *